(12) United States Patent
Grimard (10) Patent No.: US 8,087,584 B2
(45) Date of Patent: Jan. 3, 2012

(54) INVASIVE SURGICAL INSTRUMENT EQUIPPED WITH A TRANSPONDER

(75) Inventor: Jean-Christophe Grimard, Cellettes (FR)

(73) Assignee: Sferic Stellite, Menars (FR)

( * ) Notice: Subject to any disclaimer, the term of this patent is extended or adjusted under 35 U.S.C. 154(b) by 173 days.

(21) Appl. No.: 12/435,677

(22) Filed: May 5, 2009

(65) Prior Publication Data

US 2009/0277959 A1 Nov. 12, 2009

(30) Foreign Application Priority Data

May 6, 2008 (FR) ...................................... 08/02521

(51) Int. Cl.
*G06K 5/00* (2006.01)
(52) U.S. Cl. ...................... 235/380; 235/487; 340/572.8
(58) Field of Classification Search ........................ None
See application file for complete search history.

(56) References Cited

U.S. PATENT DOCUMENTS

| | | | |
|---|---|---|---|
| 6,366,206 B1* | 4/2002 | Ishikawa et al. | 340/573.1 |
| 2004/0008123 A1* | 1/2004 | Carrender et al. | 340/825.49 |
| 2005/0012617 A1* | 1/2005 | DiSilvestro et al. | 340/572.8 |
| 2005/0110638 A1* | 5/2005 | Mohr | 340/572.1 |
| 2005/0182451 A1* | 8/2005 | Griffin et al. | 607/36 |
| 2006/0214791 A1* | 9/2006 | Tethrake et al. | 340/572.1 |
| 2006/0244593 A1* | 11/2006 | Nycz et al. | 340/572.1 |
| 2006/0244652 A1* | 11/2006 | Tethrake et al. | 342/44 |
| 2007/0268133 A1* | 11/2007 | Sanchez et al. | 340/568.1 |
| 2008/0177267 A1* | 7/2008 | Sands et al. | 606/80 |

* cited by examiner

*Primary Examiner* — Steve S Paik
*Assistant Examiner* — Sonji Johnson
(74) *Attorney, Agent, or Firm* — Summa, Additon & Ashe, P.A.

(57) ABSTRACT

The present invention concerns a read system (4), and the use of the latter, which is intended to communicate with a transponder (2) placed on a surgical instrument so as to quickly identify the surgical instrument by bringing the read system (4) close to the transponder (2) of the surgical instrument and then reading the information associated with the instrument contained in the transponder (2), and communication with a computer system (5), wherein the transponder (2) is housed in a compartment (13), formed in the instrument, said compartment (13) being closed off in a sealed manner by a thin lid (14) welded or affixed (3) to the body (10) of the surgical instrument so that the outer surface of the surgical instrument has no projecting sharp points, and with the transponder (2) communicating or recording, via the read system (4), information concerning clinical history.

18 Claims, 4 Drawing Sheets

INVASIVE SURGICAL INSTRUMENT EQUIPPED WITH A TRANSPONDER

CROSS-REFERENCE TO PRIORITY APPLICATION

This application hereby claims the benefit of the commonly assigned French Patent Application Serial No. 08/02521 (filed May 6, 2008, the French Patent Office) which is hereby incorporated by reference in its entirety.

FIELD OF THE INVENTION

The invention relates to the field of surgical instrumentation. More particularly, it relates to an invasive surgical instrument, such as a femoral rasp, equipped with a transponder.

BACKGROUND

Medical instruments, and more particularly surgical instruments, are generally subjected to rigorous monitoring that is intended to guarantee their conditions of use regarding decontamination and the safety of the patients. This monitoring consists of recording and updating all useful information concerning the instrument, such as its serial number, the dates on which it was serviced or sterilised, the number of times used, etc. To this end, electronic labels, also called transponders or RFID tags (radio frequency identification tags), are used widely since they have considerable advantages. Attached to an instrument, and in association with a read and/or write module fitted with an antenna and a central computer, they can be used to write, read and store a large number of data relating to this instrument. The recording of information can be effected automatically during a cleaning operation, so as to limit human error for example. Such a method of working is described in document EP 0 992 212 for example. These electronic labels are also extremely reliable and can tolerate the high temperatures of the sterilisation procedures.

Concerning the simple metal instruments, such as scissors, scalpels, etc., the transponders are generally fixed onto a non-functional zone of the tool, such as its handle for example. In this case, they are placed in a metal container, which itself is welded to the handle.

For more complex instruments that include several parts assembled together, of which at least one is a tool, the transponder is generally attached to an outside part so as to be easy to reach for reading and writing. As an example, document EP 1 480 153 shows an endoscope formed of an invasive part, an optical coupling unit, and a control equipped with a transponder. This arrangement of the transponder on an outside part of the endoscope is not ideal, particularly in the case of partial or total dismantling of the instrument for cleaning, or for changing an element for example. In fact, once the instrument has been dismantled, the various parts and in particular the active parts are no longer identifiable. If several instruments are dismantled simultaneously, their parts can be inverted on reassembly. As a consequence, only the tracing process of the labelled part can really be guaranteed. More seriously still, incompatibility between the various parts can occur following such inversion. The operation of the instrument, and as a consequence the health of the patient, are then at risk.

From document EP 1 774 917, a medical instrument is known that includes a tubular metal element, a tool fixed to one of its ends, and means to operate the tool coupled to its other end. According to this document, the tubular element houses a passive cylindrical transponder containing information relating to the tool. However, this document concerns only a certain type of medical instrument, such as a laparoscope, which includes an interchangeable tool attached to a rod mounted inside an actuator.

Finally, document FR 2 811 923 proposes a rasp that is intended to prepare the intramedullar canal of a bone so that it can receive a prosthesis later. The rasp includes a body, lying along an axis that is substantially parallel to the longitudinal axis of the canal, of variable cross section, composed of a so-called upper face and an outer envelope, and having a shape that is designed to fit onto the inner wall of the intramedullar canal of the bone. The rasp ends in a shape that is profiled to facilitate the driving of the rasp into the canal. Male or female geometrical elements, placed on the upper face of the body, constitute a click-on system that is intended to receive an end-piece forming the end of a handle to manipulate the rasp in the canal, and that is intended to receive test prosthetic components when appropriate.

SUMMARY OF THE INVENTION

The present invention has as its objective to overcome one or more of the drawbacks of the prior art, and proposes an invasive surgical instrument, such as a femoral rasp, forming a one-piece part for which tracing can be guaranteed easily by a read system.

In order to attain this objective, a read system that is intended to cooperate with a transponder placed on the surgical instrument so as to quickly identify the surgical instrument by bringing the read system close to the transponder of the surgical instrument and then reading the information associated with the surgical instrument contained in the transponder, and by communication with a computer system, characterised in that the transponder is housed in a compartment, formed in the surgical instrument, that is intended to accommodate the transponder within it, with said compartment being closed off in a sealed manner by a thin lid of substantially the same material as the surgical instrument, welded or affixed to the body of the surgical instrument so that the outer surface of the surgical instrument has no projecting sharp points, with the transponder communicating or recording, via the read system, information concerning the clinical history, with the positions of the surgical instrument in a box being displayed on the screen of the computer system, by displaying the data coming from a database and associated with the tracing process.

According to another particular feature, the invasive surgical instrument forms a one-piece part that includes the compartment formed by a machining operation on the body of the surgical instrument in a smooth or set-back area of the body which does not weaken the surgical instrument and does not impede the fitting of a handle.

According to another particular feature, the dimensions of the compartment and the small thickness of the lid allow the transponder to be positioned close to the outer surface of the body of the surgical instrument.

According to another particular feature, the compartment and the lid are substantially cylindrical in shape.

According to another particular feature, the lid of the compartment of the surgical instrument is made from stainless steel or titanium or cobalt chrome alloy or a polymer or any other material with characteristics of resistance to corrosion and mechanical strength, with substantially the same material being used to form the body of the surgical instrument.

According to another particular feature, the lid is affixed to the surgical instrument, for example by welding, such as laser welding, electron beam welding and electrical resistance welding, so as to guarantee metallurgical continuity between the outer surface of the body of the surgical instrument and the lid, and to ensure sealing of the compartment. It will be understood that the lid may be affixed to the surgical instrument by any number of methods other than welding such as metal gluing of a sufficient strength so as to ensure metallurgical continuity between the outer surface of the body of the surgical instrument and the lid, and to ensure sealing of the compartment.

According to another particular feature, the lid is affixed to the body of the surgical instrument so as to ensure sealing of the compartment.

According to another particular feature, a read system is intended to cooperate with the transponder enclosed and held firmly in the compartment of the surgical instrument so as to allow rapid tracing of the transponder by moving the read system close to the lid of the compartment of the surgical instrument and then reading the information that is characteristic of the surgical instrument, contained in the transponder and which, after transmission from the read system to a computer system, is displayed on the screen of the computer system.

According to another particular feature, the surgical instrument is a femoral rasp that includes a body lying parallel to the longitudinal axis of the canal of the bone to be operated upon, and an upper part that is intended to be used as a means to hold and manipulate the femoral rasp, where the body of the femoral rasp includes a smooth upper zone and ends in a shape that is profiled in a taper so as to facilitate the driving of the femoral rasp into the canal of the bone, with the profiled shape of the femoral rasp including a serrated pattern that is used to rasp the canal of the bone.

According to another particular feature, the read system is designed to identify the user of the surgical instrument by means of a badge.

According to another particular feature, the computer system is a laptop personal computer.

Another objective is attained by proposing a method for incorporating a transponder into a surgical instrument according to the invention, characterised in that it includes:
  a stage for or step of machining or boring the body of the surgical instrument in order to form the compartment and then the cavity that is intended to receive the lid of the compartment of the surgical instrument;
  a stage for or step of installing of the transponder in the previously machined compartment of the surgical instrument;
  a stage for or step of installing the lid in the previously machined cavity in the body of the surgical instrument; and
  a stage for or step of affixing the thin lid to the body of the surgical instrument, so that the outer surface of the surgical instrument has no projecting sharp points.

According to another particular feature, the dimensions of the compartment and the small thickness of the lid allow the transponder to be positioned close to the outer surface of the body of the surgical instrument.

According to another particular feature, the bores created in order to form the compartment and the cavity designed to receive the lid are created on an axis that is perpendicular to the outer surface of the body of the surgical instrument.

According to another particular feature, the diameter of the bore forming the compartment is less than the diameter of the bore forming the cavity for the lid, and the depth of the bore forming the compartment is greater than the depth of the bore forming the cavity for the lid.

According to another particular feature, the diameter and the depth of the compartment formed by machining are respectively somewhat greater than the diameter and the depth of the transponder, so that the transponder is held firmly in the compartment when the lid is affixed to the body of the surgical instrument, for example, by welding.

Another objective is attained by proposing the use of a surgical instrument according to the invention, wherein the surgical instrument is intended to cooperate with a read system connected to a computer system managing a database, where this use includes:
  a stage for or step of reading the information contained in the transponder, held firmly in the compartment of the surgical instrument, by means of the read system;
  a stage for or step of transmitting the information read by the read system for sending to the computer system;
  a stage for or step of searching, by means of an appropriate application in the computer system, in the database of the computer system for the tracing data associated with the surgical instrument; and
  a stage for or step of displaying, on the screen or interface of the computer system, the location of the surgical instrument in the storage container and the tracing data associated with the surgical instrument, such as the storage container number, the number of the compartment of the surgical instrument in said container, the number of the surgical instrument, and the clinical history associated with the surgical instrument or the data relating to the patients or the operating data relating to previous surgical interventions.

According to another particular feature, the computer data associated with the surgical instrument and displayed on the screen of the computer system can be selected by the user via a user interface of the computer system, and can provide information on the conditions of use, and on the cleaning, sterilisation and storage conditions of the surgical instrument.

According to another particular feature, the tracing data associated with the surgical instrument are designed to be modified simultaneously with the use of the surgical instrument, with the changes being entered by means of the interface of the computer system and then retransmitted via the read system to the transponder so that they can be stored in the transponder.

According to another particular feature, the tracing data associated with the surgical instrument can be modified simultaneously with the use of the surgical instrument, with the changes being entered by means of the user interface of the computer system and then retransmitted via the read system to the transponder so that they can be stored in the memory of the transponder.

According to another particular feature, the tracing data associated with the surgical instrument, once transmitted to the computer system, can be transmitted over the Internet to the manufacturer and/or to the establishment to which the surgical instrument is delivered.

According to another particular feature, an audio alarm of the computer system indicates any wear on the surgical instrument and gives notice of the purchase of a new surgical instrument.

In view of the motor vehicle seats of the type mentioned herein above, the object of the present invention is to further develop the prior art motor vehicle seat in such a manner that the seat portion is capable of extending and retracting such that the seat portion varies proportionally in size.

BRIEF DESCRIPTION OF THE DRAWINGS

The foregoing and other objects and advantages of the invention and the manner in which the same are accomplished will become clearer based on the following detailed description taken in conjunction with the accompanying drawings in which.

DETAILED DESCRIPTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The invention concerns a surgical instrument forming a one-piece part, such as a femoral rasp (1), equipped with a transponder (2).

The remainder of the description makes reference to a femoral rasp (1) for hip prostheses, but the invention applies to any surgical instrument forming a one-piece part.

The femoral rasp (1), equipped with such a transponder (2), advantageously brings an improvement to the monitoring or tracing of the latter between the various health establishments and its management, such as use on certain patients, the management of stocks, etc., for example.

Figure 1:
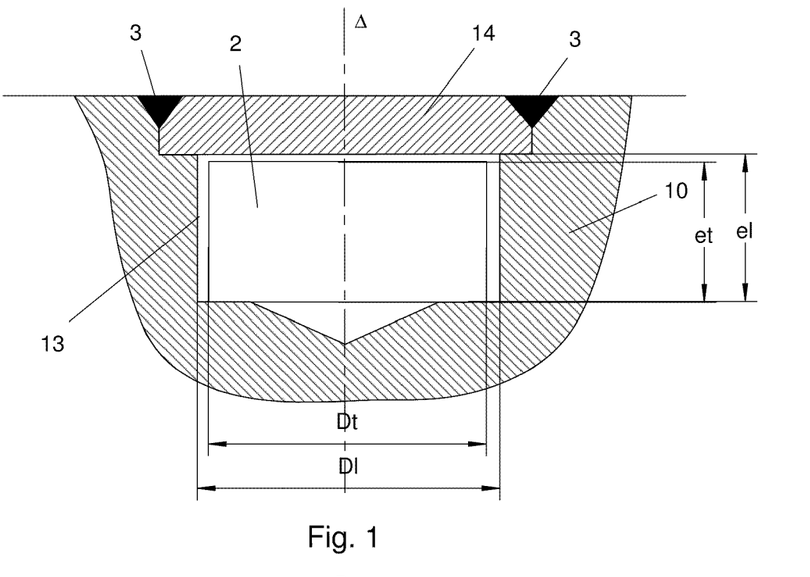
FIG. 1 represents a longitudinal view in section of one part of the body of a surgical instrument, such as a femoral rasp, equipped with a transponder placed in a machined compartment.
Figure 2:
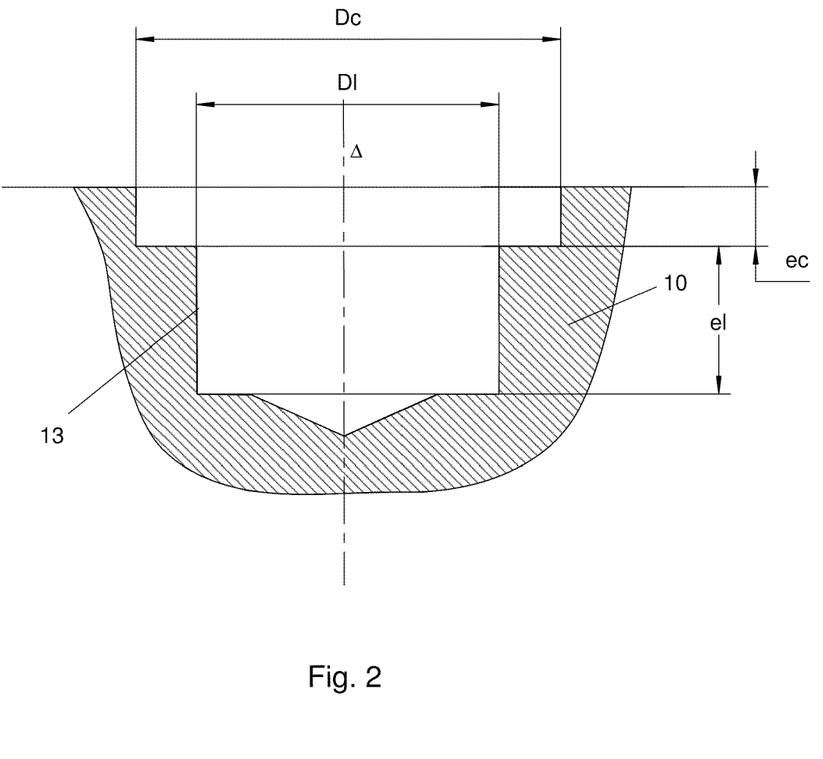
FIG. 2 represents a longitudinal view in section of one part of the body of a surgical instrument, such as a femoral rasp, in which a compartment has been machined to receive a transponder.
Figure 3:
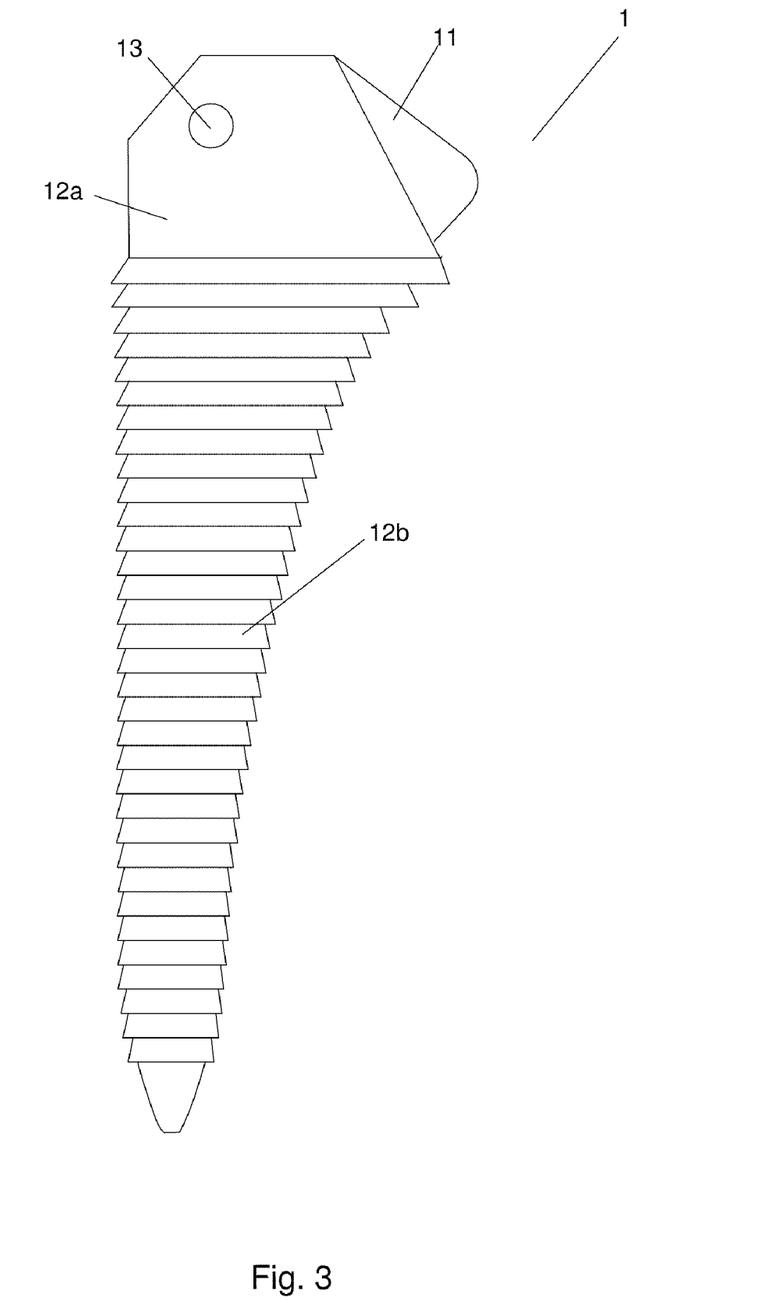
FIG. 3 represents a view in section of a femoral rasp equipped with a compartment that is intended to receive a transponder.

The femoral rasp (1) represented in FIGS. 1 to 3, conventionally includes a body (10) lying parallel to the longitudinal axis of the canal of the bone to be operated upon. The femoral rasp (1) includes an upper part (11) that is intended to be used as a means to hold and manipulate the femoral rasp (1). The body (10) of the femoral rasp (1) includes a smooth top zone (12a) and ends in a shape that is profiled (12b) in a taper in order to facilitate the driving of the femoral rasp (1) into the canal of the bone. The profiled shape (12b) of the body (10) of the femoral rasp (1) includes a serrated pattern that is used to rasp the canal of the bone. It should be noted that the femoral rasp (1) forms a one-piece part.

In addition, the femoral rasp (1) is characterised in that it is made from an inoxidizable material such as stainless steel or TA6V titanium or a cobalt chrome alloy or a polymer for example.

The geometrical shape of the femoral rasp (1) is particular and depends on the prosthesis or the implant to be inserted into the canal of the bone previously rasped by means of the femoral rasp (1).

The femoral rasp (1) includes a compartment (13) formed by a machining or boring operation on the body (10) of the femoral rasp (1) in the smooth top zone (12a) or in a zone that is set back in relation to the serrations of the profiled shape (12b) of the body (10) of the femoral rasp (1) so as not to weaken the femoral rasp (1).

In the example represented in FIG. 3, the compartment (13) is created in the smooth top zone (12a) of the body (10) of the femoral rasp (1).

The compartment (13), which is substantially cylindrical in shape and opening onto the smooth outer surface of the rasp (1), is intended to receive inside it a transponder (2) or an electronic label or indeed an RFID tag, and then is closed off in a sealed manner by a thin lid (14) that is affixed at various positions (3) (e.g., by welding or other means) to the body (10) of the femoral rasp (1) so that the outer surface of the femoral rasp (1) has no projecting sharp points.

In fact, since the femoral rasp (1) is an invasive surgical instrument, it is absolutely necessary that the latter returns to its initial shape before the machining of the compartment (13) in the body (10).

In a manner that is not limiting, the lid (14), of substantially cylindrical shape, of the compartment (13) in the rasp (1), is made from stainless steel or titanium or cobalt chrome alloy or a polymer or any other material that possesses characteristics of resistance to corrosion and mechanical strength.

The small thickness of the lid (14) and the dimensions of the compartment (13) advantageously allow the transponder (2) to be positioned quite close to the outer surface of the body (10) of the femoral rasp (1) so that the information contained in the transponder (2) can be read easily.

It should be noted that the substantially same material will be used to form the body (10) of the rasp (1) and the lid (14) of the compartment (13) in the rasp (1).

In a manner that is not limiting, the operation for affixing (e.g., by welding) the lid (14) to the body (10) of the rasp (1) at various positions (3) may be performed by a laser, without affecting the operation of the transponder (2), so as to guarantee metallurgical continuity between the outer surface of the body (10) of the rasp (1) and the lid (14). It will be understood that the operation of affixing the lid (14) to the body (10) of the rasp (1) may be accomplished by any other welding method that will guarantee this metallurgical continuity.

The affixing operation advantageously seals the compartment (13) of the femoral rasp (1) so as not to affect the transponder (2) and the information that it contains during the sterilisation operations of the femoral rasp (1) for example, or any other operations involving the cleaning or use of the femoral rasp (1), etc. In fact, the transponder (2) is resistant to the sterilisation operations performed at high temperatures, such as 135° C., but is not resistant to humidity. As a consequence, it is necessary that the compartment (13) formed in the body (10) of the femoral rasp (1) should be sealed in order to protect the transponder (2) from humidity and liquids.

It should be noted that the transponder (2) can tolerate maximum temperatures of about 250° C.

It should also be noted that only one transponder (2) is inserted into the compartment (13) formed in the femoral rasp (1).

The transponder (2) thus inserted into its compartment (13) is advantageously protected from mechanical shock during use and cleaning of the femoral rasp (1).

These passive cylindrical transponders (2) are known to the person skilled in the art. They are employed for the marking of objects. The transponders (2) include an electronic circuit that is equipped with two contact pads and a coil formed by a wire wound onto a ferrite core and whose ends are welded to the contact pads. Reading from and writing to these transponders (2) is effected by means of the antenna formed by the annular winding designed to emit and receive a radio frequency (RF) signal containing information (serial number, dates of maintenance or sterilisation operations, etc.), and a central computer that is intended to store and process the information obtained from the RF signal.

Figure 5:
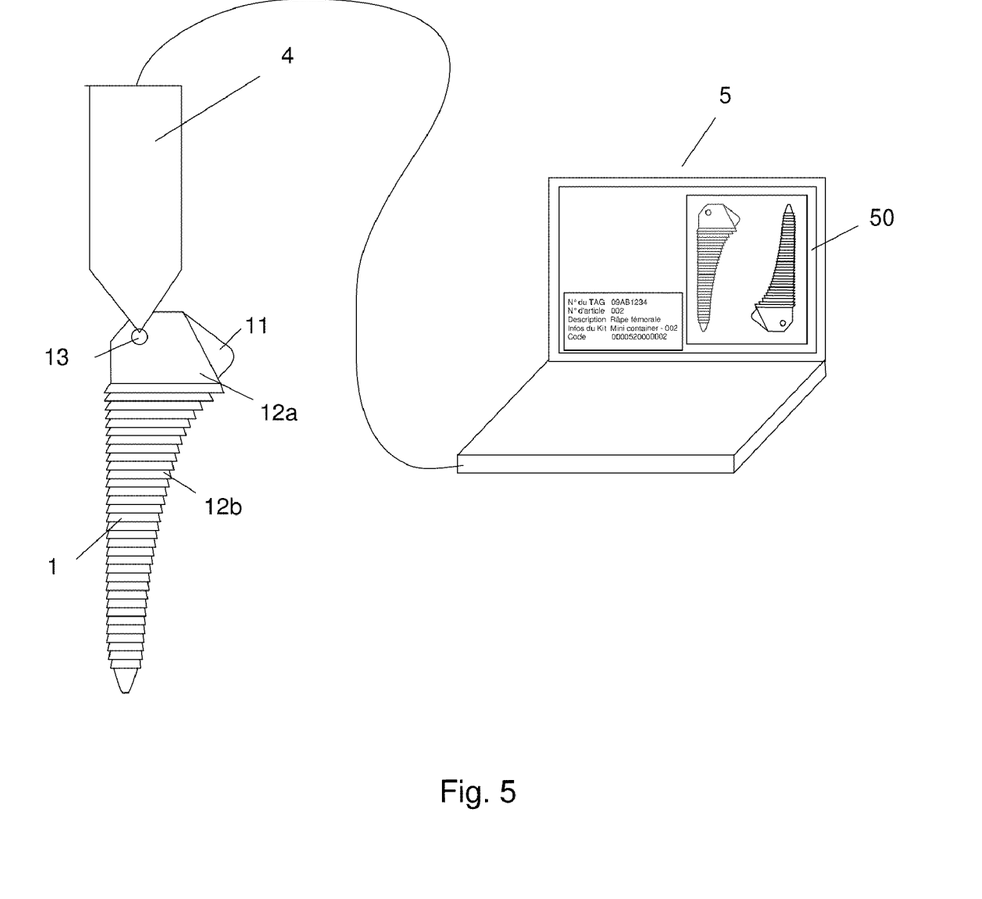
FIG. 5 illustrates the use of the surgical instrument working with a read system associated with a computer system.

Referring to FIG. 5, the present invention also proposes the use of the surgical instrument, such as a femoral rasp (1), equipped with a transponder (2), with the surgical instrument being intended to cooperate with a read system (4) connected to a computer system (5).

The use of the surgical instrument includes:

a stage for or step of reading the information contained in the transponder (2) held firmly in the compartment (13) of the surgical instrument by means of the read system (4);

a stage for or step of transmitting the information read by the read system (4) intended for the computer system (5);

a stage for or step of searching in the database, by means of an appropriate application in the computer system (5), for the tracing data associated with the surgical instrument; and a stage for or step of displaying, on the interface (50) of the computer system (5), the location of the surgical instrument in the storage container and the tracing data associated with the surgical instrument.

The display stage provides access to the tracing data associated with the surgical instrument, such as the storage container number, the number of the compartment of the surgical instrument in said container, the number of the surgical instrument, the clinical history associated with the surgical instrument, the data relating to the patients and the operating data of the previous surgical interventions.

The computer data associated with the surgical instrument and displayed on the interface (50) of the computer system (5) can be selected by the user via a user interface such as a keyboard or a mouse connected to the computer system (5), and can provide information on the conditions of use, cleaning, sterilisation and storage of the surgical instrument. The computer data can be stored in the system itself or can be associated with a remote server via an Internet connection, for example. The computer data can therefore be updated remotely.

The read stage of the transponder (2) of the surgical instrument consists either of approaching with the read system (4) which, using a short-distance electronic sensor positioned at about 2 to 3 millimeters from the lid (14) of the compartment (13) of the femoral rasp (1), is able to read the information contained in the transponder (2) and associated with the surgical instrument, or of connecting the read system (4) to the transponder (2) by means of a read probe which is able to read the information contained in the transponder (2) and associated with the surgical instrument. The information acquired by the read system (4) is sent to the computer system (5) which, using an appropriate application, performs the search stage in the database. This information or tracing data associated with the surgical instrument can then, as appropriate, be advantageously transmitted over the Internet to the manufacturer and/or to the establishment to which the surgical instrument is delivered, with this exchange acting as a transfer record.

In addition, the tracing data associated with the surgical instrument can be modified simultaneously with the uses of the surgical instrument, including the data associated with the last surgical intervention for example, like the name of the last patient, the name of the surgeon, or the name of the health establishment. These changes are entered by means of the user interface of the computer system (5), such as via the keyboard, and then retransmitted via the read system (4) to the transponder (2) so that they can be stored in the memory of the transponder (2). The data stored in the memory of the transponder (2) are advantageously rewriteable.

The management of the surgical instrument can be accomplished by the responsible service of a hospital or a remote relevant company.

The computer system (5) can be a personal computer for example, that includes at least the means to access a server via a communication network and a user interface.

The read system and computer system assembly can advantageously be a laptop personal computer. It can be installed and used directly in the operating theatre or in adjoining rooms for preparation, monitoring, cleaning, sterilisation, and conditioning of the instruments. The operatives who execute these tasks are also able to use the same read system in order to identify themselves by means of a badge. The name of the participants can thus be recorded and stored in an associated database.

It should be noted that the location of the surgical instrument in the storage container is displayed, with highlighting for example, on the interface (50) of the computer system (5).

The read system (4) connected to the computer system (5) can advantageously be used not only by pharmacy staff in order to check the receipt of each surgical instrument for example, or to ascertain the clinical history, manage the stocks, monitor each surgical instrument, or predict purchase orders, but also by the staff responsible for sterilisation in the health establishments in order, for example, to quickly reconstitute the boxes of medical instruments after the surgical intervention and decontamination of all the medical instruments. This read system (4) associated with the computer system (5) and used with the surgical instrument, such as the femoral rasp (1), advantageously saves time during the tracing process or the retrieval of information associated with the surgical instrument, and allows efficient management of a surgical instrument recall or a patient recall. In addition, during the reading of the transponder (2) of the surgical instrument, it is possible for an audio alarm from the computer system (5) to inform the user of wear on the surgical instrument and, as a consequence, to arrange for the purchase of a new surgical instrument.

Figure 4:
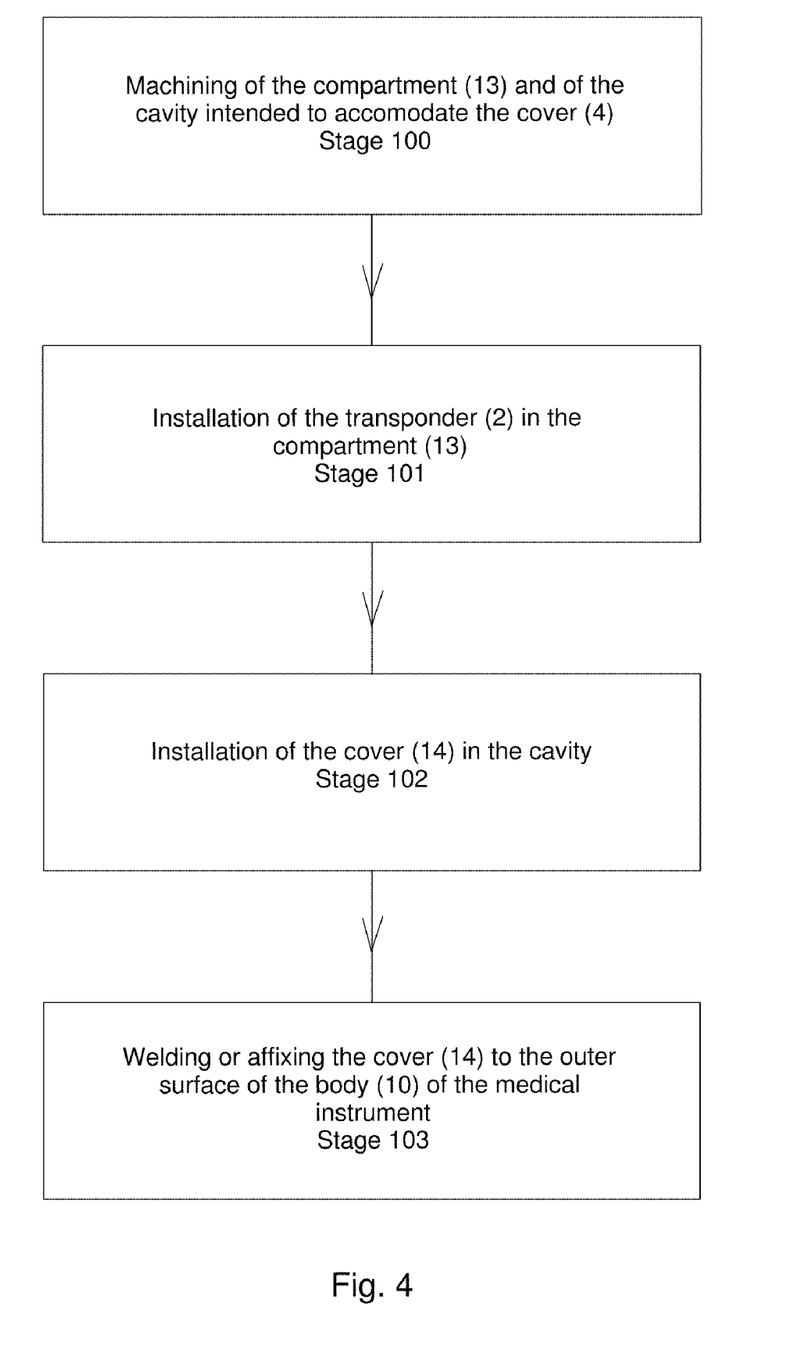
FIG. 4 illustrates the method for incorporating a transponder into a surgical instrument formed of a one-piece part.

Referring to FIG. 4, the method for incorporating the transponder (2) into the femoral rasp (1) consists of performing a machining or boring operation (stage 100) in order to form the compartment (13) of substantially cylindrical shape and then the cavity of substantially cylindrical shape that is intended to receive the thin lid (14) of the compartment (13) in the femoral rasp (1).

The boring operations in order to form the compartment (13) and the cavity designed to receive the lid (14) are effected on an axis ($\Delta$) that is perpendicular to the outer surface of the body (10) of the femoral rasp (1).

It should be noted that the diameter (Dl) of the bore forming the compartment (13) is less than the diameter (Dc) of the bore forming the cavity for the lid (14). In addition, the thickness or the depth (el) of the bore forming the compartment (13) is greater than the depth (ec) of the bore forming the cavity for the lid (14).

According to the smooth zone of the body (10) of the rasp (1) that is machined, and the dimensions of the transponder (2), the bore created in order to form the compartment (13) must be executed with a depth (el) and a diameter (Dl) that are determined so as not to adversely affect the femoral rasp (1) and to allow the positioning of the transponder (2) quite close to the outer surface of the body (10) of the femoral rasp (1).

In a first implementation example, for a transponder (2) of a diameter (Dt) of about 5.6 millimeters and a thickness (et) of about 1.7 millimeters, a bore of a diameter (Dl) of about 6.6 millimeters and of a depth (el) of about 1.9 millimeters is created. It should be noted that the nose of the drill bit used for the bore in order to form the compartment (13) must not exceed a diameter of about 4.5 millimeters, so as not to weaken or adversely affect the femoral rasp (1).

In a second implementation example, for a transponder (2) of a diameter (Dt) of about 7.4 millimeters and a thickness (et) of about 2.6 millimeters, a bore of a diameter (Dl) of about 7.5 millimeters and of a depth (el) of about 2.7 millimeters is created. It should be noted that the nose of the drill bit used for the bore in order to form the compartment (13) must not exceed a diameter of about 6.5 millimeters, so as not to weaken or adversely affect the femoral rasp (1).

As a consequence, the diameter (Dl) and the depth (el) of the compartment (13) formed by the machining operation are respectively somewhat greater than the diameter (Dt) and the depth (et) of the transponder (2).

The small difference between the diameters (Dl, Dt) and the depths (el, et) of the compartment (13) and the transponder (2) respectively, advantageously allow the transponder (2) to be held firmly in the compartment (13) when the lid (14) is welded or affixed to the body (10) of the femoral rasp (1).

Once the transponder (2) is positioned or held firmly in the compartment (13) (stage 101), the method for incorporating the transponder (2) in the femoral rasp (1) includes a stage for positioning (stage 102) the lid (14) in the cavity designed to receive said lid (14), and then an operation (stage 103) to affix the lid (14) to the body (10) of the femoral rasp (1) by any number of means so that the outer surface of the rasp (1) has no projecting sharp points.

One of the advantages of the invention is that the surgical instrument equipped with a transponder (2) enables it to be identified and traced individually while still retaining these invasive properties.

In another embodiment, the invention is a system for collecting, storing, and updating data. The system comprises a surgical instrument (10) having an outer surface and defining a compartment (13), a transponder (2) affixed to the surgical instrument (10) for receiving and emitting data unique to the surgical instrument, a computer system (5) for storing the data, and a read system (4) providing communication between the transponder (2) and the computer system (5).

Advantageously the system permits a user to collect, store, update, and transmit the data unique to the surgical instrument (10) across multiple lines of communication to a plurality of interfaces.

The system further comprises a lid (14) having an exterior surface, wherein the lid secures the transponder (2) within the surgical instrument (10). In one embodiment, the exterior surface of the lid (14) is substantially planar with respect to the outer surface of the surgical instrument (10) to thereby seal the transponder (2) within the surgical instrument (10).

As configured and illustrated in FIGS. 1 and 2, a diameter of the compartment (13) is less than a diameter of the lid (14) in order to secure the transponder within the surgical instrument (10). The compartment (13) is formed in a smooth portion of the outer surface of the surgical instrument (10) to facilitate use thereof. The transponder (2) is positioned substantially adjacent to the lid (14) to thereby promote communication between the transponder (2) and read system (4).

It should be obvious the person skilled in the art that the present invention allows embodiments in many other specific forms without moving outside the field of application of the invention as claimed. As a consequence, the present embodiments should be considered as being provided by way of illustration only, and capable of modification within the field defined by the scope of the attached claims, and the invention must not be limited to the details provided above.

In the drawings and specification, there have been disclosed typical embodiments on the invention and, although specific terms have been employed, they have been used in a generic and descriptive sense only and not for purposes of limitation, the scope of the invention being set forth in the following claims.

The invention claimed is:

1. A read system (4) that is intended to cooperate with a transponder (2) placed on a surgical instrument having a body (10), so as to quickly identify the surgical instrument by bringing the read system (4) close to the transponder (2) of the surgical instrument and then reading the information, associated with the surgical instrument, contained in the transponder (2), and by communication with a computer system (5), wherein the transponder (2) is housed in a compartment (13), formed in the surgical instrument, which is intended to accommodate the transponder (2) within it, with said compartment (13) being closed off in a sealed manner by a lid (14), of substantially the same material as the surgical instrument, affixed (3) to the body (10) of the surgical instrument, the lid being housed in contact with a cavity, so that an outer surface of the body (10) of the surgical instrument has no projecting sharp points, with the transponder (2) communicating or recording, via the read system (4), information concerning a clinical history, with various positions of the surgical instrument in a box being displayed on the screen of the computer system (5) by displaying the data coming from a database and associated with a tracing process, the invasive surgical instrument forming a one-piece part that includes the compartment (13) formed by a machining operation in the body (10) of the surgical instrument in a smooth or set-back area of the body (10), which does not weaken the surgical instrument and does not impede the fitting of a handle, the lid (14) being affixed to the surface of the cavity of the body (10) of the surgical instrument so as to ensure sealing of the compartment (13), the diameter of the bore forming the compartment is less than the diameter of the bore forming the cavity of the lid.

2. A read system (4) according to claim 1, wherein dimensions of the compartment (13) and the lid (14) allow the transponder (2) to be positioned close to the outer surface of the body (10) of the surgical instrument.

3. A read system (4) according to claim 1, wherein the compartment (13) and the lid (14) are substantially cylindrical in shape.

4. A read system (4) according to claim 1, wherein the lid (14) of the compartment (13) and the body (1) of the surgical instrument are made from substantially the same material that exhibits characteristics of resistance to corrosion and mechanical strength.

5. A read system (4) according to claim 1, wherein the material forming the lid (14) of the compartment (13) and the body (1) of the surgical instrument is selected from the group consisting of stainless steel, titanium, cobalt chrome alloy, and a polymer.

6. A read system (4) according to claim 1, wherein the lid (14) is affixed to the body (10) of the surgical instrument by welding so as to guarantee metallurgical continuity between the outer surface of the body (10) of the surgical instrument and the lid (14), and to ensure sealing of the compartment (13).

7. A read system (4) according to claim 1, wherein the surgical instrument is a femoral rasp (1) having a body (10) lying parallel to the longitudinal axis of a canal of a bone to be operated upon, and an upper part (11) that is used as a means to hold and manipulate the femoral rasp (1), the body (10) of the femoral rasp (1) having a smooth upper zone (12a) and ends in a shape that is profiled (12b) in a taper in order to facilitate the driving of the femoral rasp (1) into the canal of the bone, and where the profiled shape (12b) of the femoral rasp (1) having a serrated pattern that is used to rasp the canal of the bone.

8. A read system (4) according to claim 1, wherein the read system is designed to identify the user of the surgical instrument by means of a badge.

9. A read system (4) according to claim 1, wherein the computer system is a laptop personal computer.

10. A system for collecting, storing, and updating data, the system comprising:
- a surgical instrument (10) having an outer surface and defining a compartment (13);
- a transponder (2) affixed to the surgical instrument (10), the transponder for receiving and emitting data unique to the surgical instrument;
- a computer system (5) for storing the data;
- a read system (4) providing communication between the transponder (2) and the computer system (5); and
- a lid (14) having an exterior surface and being housed in contact with a cavity, the lid securing the transponder (2) within the surgical instrument (10), the exterior surface of the lid (14) substantially planar with respect to the outer surface of the surgical instrument (10) to seal the transponder (2) within the surgical instrument (10);
- wherein the invasive surgical instrument forms a one-piece part that includes the compartment (13) formed by a machining operation in the body (10) of the surgical instrument in a smooth or set-back area of the body (10), which does not weaken the surgical instrument and does not impede the fitting of a handle, the lid (14) being affixed to the surface of the cavity of the body (10) of the surgical instrument so as to ensure sealing of the compartment (13), the diameter of the bore forming the compartment being less than the diameter of the bore forming the cavity of the lid; and
- wherein the system permits a user to collect, store, update, and transmit the data unique to the surgical instrument (10) across multiple lines of communication to a plurality of interfaces.

11. The system according to claim 10, wherein: the compartment (13) is formed in a smooth portion of the outer surface of the surgical instrument (10) to facilitate use thereof; and the transponder (2) is positioned substantially adjacent to the lid (14) to thereby promote communication between the transponder (2) and the read system (4).

12. A surgical instrument having a transponder that cooperates with a read system (4) so as to quickly identify the surgical instrument by bringing the read system (4) close to the transponder (2) of the surgical instrument and then reading the information, wherein the transponder (2) is housed in a compartment (13), formed in the surgical instrument, which is intended to accommodate the transponder (2) within it, with said compartment (13) being closed off in a sealed manner by a thin lid (14), of the same material as the surgical instrument, welded or affixed (3) to the body (10) of the surgical instrument, the lid being housed in contact with a cavity, so that the outer surface of the surgical instrument has no projecting sharp points, the invasive surgical instrument forming a one-piece part that includes the compartment (13) formed by a machining operation in the body (10) of the surgical instrument in a smooth or set-back area of the body (10), which does not weaken the surgical instrument and does not impede the fitting of a handle, the lid (14) being affixed to the surface of the cavity of the body (10) of the surgical instrument so as to ensure sealing of the compartment (13), the diameter of the bore forming the compartment is less than the diameter of the bore forming the cavity of the lid.

13. A surgical instrument according to claim 12, wherein the dimensions of the compartment (13) and the small thickness of the lid (14) allow the transponder (2) to be positioned close to the outer surface of the body (10) of the surgical instrument.

14. A surgical instrument according to claim 12, wherein the compartment (13) and the lid (14) are substantially cylindrical shape.

15. A surgical instrument according to claim 12, wherein the lid (14) of the compartment (13) and the body of the surgical instrument are made from a material that exhibits characteristics of resistance to the corrosion and mechanical strength.

16. A surgical instrument according to claim 12, wherein the material forming the lid (14) of the compartment (13) and the body of the surgical instrument is selected from the group consisting of stainless steel or titanium or cobalt chrome alloy or a polymer.

17. A surgical instrument according to claim 12, wherein the lid (14) is attached by welding, such as laser welding, so as to guarantee metallurgical continuity between the outer surface of the body (10) of the surgical instrument and the lid (14), and to ensure sealing of the compartment (13).

18. A surgical instrument according to claim 12, wherein the surgical instrument is a femoral rasp (1) that includes a body (10) lying parallel to the longitudinal axis of the canal of the bone to be operated upon, and an upper part (11) that is intended to be used as a means to hold and manipulate the femoral rasp (1), where the body (10) of the femoral rasp (1) includes a smooth upper zone (12a) and ends in a shape that is profiled (12b) in a taper in order to facilitate the driving of the femoral rasp (1) into the canal of the bone, and where the profiled shape (12b) of the femoral rasp (1) includes a serrated pattern that is used to rasp the canal of the bone.

* * * * *

UNITED STATES PATENT AND TRADEMARK OFFICE
CERTIFICATE OF CORRECTION

| | | |
|---|---|---|
| PATENT NO. | : 8,087,584 B2 | Page 1 of 1 |
| APPLICATION NO. | : 12/435677 | |
| DATED | : January 3, 2012 | |
| INVENTOR(S) | : Jean-Christophe Grimard | |

It is certified that error appears in the above-identified patent and that said Letters Patent is hereby corrected as shown below:

On the title page of the patent the following cited references were omitted:

FOREIGN PATENT DOCUMENTS

EP 0992212  4/2000

EP 1480153  11/2004

EP 1774917  4/2007

FR 2811923  1/2002

Signed and Sealed this
Thirteenth Day of November, 2012

David J. Kappos
*Director of the United States Patent and Trademark Office*